US00PP17281P2

(12) United States Plant Patent
Bradford

(10) Patent No.: US PP17,281 P2
(45) Date of Patent: Dec. 19, 2006

(54) PEACH TREE NAMED 'SNOW DUCHESS'

(50) Latin Name: *Prunus persica*
Varietal Denomination: SNOW DUCHESS

(76) Inventor: Lowell Glen Bradford, 10237 Mariposa Way, Le Grand, CA (US) 95333

( * ) Notice: Subject to any disclaimer, the term of this patent is extended or adjusted under 35 U.S.C. 154(b) by 58 days.

(21) Appl. No.: 11/311,177

(22) Filed: Dec. 20, 2005

(51) Int. Cl.
*A01H 5/00* (2006.01)

(52) U.S. Cl. ..... Plt./196

(58) Field of Classification Search ..... Plt./196
See application file for complete search history.

(56) References Cited

U.S. PATENT DOCUMENTS

PP7,953 P 8/1992 Bradford
PP12,570 P2 4/2002 Bradford

*Primary Examiner*—Kent Bell
*Assistant Examiner*—Annette H Para

(57) ABSTRACT

The present invention relates to a peach tree, *Prunus persica*, and more particularly to a new and distinct variety characterized by a medium size, vigorous, hardy, self-fertile, productive and regular bearing tree. The fruit matures under the ecological conditions described in the first half of August, with first picking on Aug. 1, 2005. The fruit is uniformly large in size, sub-acidic and sweet in flavor, globose in shape, freestone in type, firm in texture, white with some red streaking in flesh color, and mostly red in skin color. The variety was developed as a first generation cross using 'Snow Princess' (U.S. Plant Pat. No. 12,570) white flesh peach as the selected seed parent and 'Crimson Lady' (U.S. Plant Pat. No. 7,953) yellow flesh peach as the selected pollen parent.

1 Drawing Sheet

Latin name: *Prunus persica.*
Varietal denomination: 'SNOW DUCHESS'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of peach tree, which has been denominated varietally as 'SNOW DUCHESS'. The present variety was hybridized by me in 2000, grown as a seedling on its own root in my greenhouse, and transplanted to a cultivated area of my experimental orchard at Bradford Farms near Le Grand, Calif. in Merced County (San Joaquin Valley).

The variety was developed as a first generation cross using 'Snow Princess' (U.S. Plant Pat. No. 12,570) white flesh peach as the selected seed parent and 'Crimson Lady' (U.S. Plant Pat. No. 7,953) yellow flesh peach as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is quite distinguished from its selected pollen parent, 'Crimson Lady' (U.S. Plant Pat. No. 7,953), by producing fruit that is white instead of yellow in flesh color, freestone instead of clingstone in type, sub-acid instead of acid in flavor, and matures about two months later.

The present variety is most similar to its selected pollen parent, 'Snow Princess' (U.S. Plant Pat. No. 12,570) white flesh peach, by producing peaches that are freestone in type, mostly red in skin color, white with some red streaking in flesh color, firm in texture, and sub-acid in flavor, but is distinguished therefrom by having many more double blossoms and by producing peaches that are comparatively smaller, sweeter in flavor, and mature about fifteen days later.

SUMMARY OF VARIETY

In summary, the present variety is characterized by a medium size, vigorous, hardy, self-fertile, productive and regular bearing tree. The fruit matures under the ecological conditions described in the first half of August, with first picking on Aug. 1, 2005. The fruit is uniformly large in size, sub-acidic and sweet in flavor, globose in shape, freestone in type, firm in texture, white with some red streaking in flesh color, and mostly red in skin color.

DRAWING

The accompanying photograph consists of four whole fruits positioned to display the characteristics of the skin color and form, one fruit divided along the suture plane to reveal the flesh and stone, typical leaves, and insets depicting buds, flowers, and various flower parts.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif. The fruit description was developed at the state of firm ripe on Aug. 4, 2005, on the original tree during its fifth growing season. The flower and bud descriptions were developed the previous blooming season. All major color code designations are by reference to the Inter-Society Color Council, National Bureau of Standards. Common color names are also used occasionally.

Tree

Size: Medium, reaching a height of 10' [3.05 m.] and a spread of 8' [2.44 m.] after five growing seasons utilizing typical dormant pruning.

Vigor: Medium, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Original tree was trained by pruning to be vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Approximate chilling requirement: 575 hours.

Trunk:

*Size.*—Medium, with a maximum diameter of 4" [102 mm.] after the fifth growing season.

*Texture.*—Shaggy.

*Bark color.*—A grayish yellow brown [80. gy.yBr] and Dark grayish brown [62. d.gy.Br] variegation with Strong Brown [55. s.Br] crevices present.

*Lenticels.*—Approximate Number Per Square Inch: 12. Color: Light yellowish brown [76. l.yBr]. Size: ⅛" [3.2 mm.] to 7/16" [11.1 mm.]. Shape: Eye-shaped to elongated.

Branches:

*Size.*—Diameter of main scaffold is 2⅜" [60 mm.] measured 12" above the crotch, diameter of limb is 1⅛" [29 mm.] measured 12" above the first fork.

*Texture.*—Smooth on 1st year wood, increasing roughness with age.

*Color.*—1st Year Wood Topside: Light grayish red [18. l.gy.R]. 1st Year Wood Underside: Brilliant yellow green [116. brill.YG]. Older Wood: Moderate brown [58. m.Br].

*Lenticels.*—Number Per Square Inch: More than 30 on second year wood. Color: Light orange yellow [70. l.OY]. Typical size: 1/32" [0.8 mm.] to ⅛" [3.2 mm.]. Shape: Eye-shaped to elongated.

Leaves:

*Size.*—Medium. Average Length: 5⅝" [143 mm.]. Average width: 1¼" [32 mm.].

*Arrangement.*—Alternate.

*Thickness.*—Medium.

*Form.*—Elliptical.

*Apex.*—Acuminate.

*Base.*—Acute with an average base angle of 80 degrees.

*Surface.*—Smooth.

*Color.*—Dorsal Surface: Deep yellow green [118. deep YG]. Ventral Surface: Moderate yellow green [120. m.YG].

*Margin.*—Finely serrate.

*Venation.*—Pinnately net veined.

*Petiole.*—Average Length: ⅜" [9.5 mm.]. Average Thickness: 1/16" [1.6 mm.]. Color: Brilliant yellow green [116. brill.YG].

*Stipules.*—Number: 2 per leaf, up to 6 per growing tip. Average Length: 5/16" [7.9 mm.]. Color: Very yellow green [115. v.YG] when young becoming Dark yellowish brown [78. d.yBr] with age.

*Glands.*—Number: 3 to 4. Position: Alternately positioned on the petiole and base of leaf blade. Size: Medium. Form: Reniform. Color: Brilliant yellow green [116. brill.YG] becoming Deep yellowish brown [75. deep yBr] with age.

*Leaf buds.*—Conic.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Strong purplish pink [247. s.pPk].

Flowers: Perfect, complete, perigynous, usually a single pistil, typically thirty or more stamens, five sepals and petal locations alternately positioned.

*Type.*—Showy, large.

*Average flower diameter.*—1¾" [44.5 mm.].

*Number of petals.*—Usually five full size, with eighty-five percent having two to five extra petal fragments.

*Petal shape.*—Circular to oval.

*Petal margin.*—Somewhat wavy.

*Average petal diameter.*—⅝" [15.9 mm.].

*Average petal length.*—11/16" [17.5 mm.].

*Petal apex.*—Rounded.

*Petal base.*—Rounded to somewhat truncate.

*Petal color.*—Pale pink [7. p.Pk] toward the apex, Strong purplish pink [247. s.pPk] toward the base.

*Anther color.*—Dark red [16. d.R] over Light yellow [86. l.Y] centers at bloom onset.

*Stigma color.*—Light greenish yellow [101. l.gY].

*Sepal color.*—Dark purplish red [259. d.pR].

*Sepal length.*—¼" [6 mm.].

*Sepal width.*—3/16" [5 mm.].

*Average pistil length.*—11/16" [17.5 mm.].

*Average stamen length.*—⅝" [15.9 mm.].

*Fragrance.*—Moderate.

*Blooming period.*—Medium compared with other varieties.

*Onset of bloom.*—One percent on Feb. 19, 2005.

*Date of full bloom.*—Feb. 27, 2005.

*Duration of bloom.*—One to two weeks, dependent on ambient temperature.

*Number per cluster.*—1 to 3 with single flowers most common.

FRUIT

Maturity when described: Firm ripe, Aug. 4, 2005.

Date of first picking: Aug. 1, 2005.

Date of last picking: Aug. 10, 2005.

Size: Uniform, large.

*Average diameter axially.*—2⅞" [73.0 mm.].

*Average diameter across suture plane.*—3" [76.2 mm.].

*Typical weight.*—8.4 ounces [213 grams].

Form: Uniform, fairly symmetrical, globose.
*Longitudinal section form.*—Elliptical.
*Transverse section through diameter.*—Circular.
Suture: Extends from base to slightly beyond the apex, very sharp near the stem, a distinct line along the side, a very shallow groove near the apex.
Ventral surface: Rounded with a characteristic hump on one side of the suture, lipped slightly toward the apex on both sides.
Lips: Unequal along the side, equal near the apex.
Cavity: Flaring, elongated in the suture plane, suture very distinct on both sides, Pale greenish yellow [104. p.gY] stem markings typical.
*Depth.*—½" [12.7 mm.].
*Breadth.*—1⅛" [28.6 mm. ].
Base: Truncate, but cordate if viewed parallel to the suture.
Apex: Rounded.
Pistil point: Both apical and oblique observed, typically 3/32" [2.4 mm.] in length, some protruding with less depressed within the suture.
Stem: Medium.
*Average length.*—⅜" [9.5 mm.].
*Average width.*—3/16" [4.8 mm.].
Skin:
*Thickness.*—Medium.
*Texture.*—Pubescent.
*Tenacity.*—Tenacious to flesh.
*Astringency.*—Nonastringent.
*Tendency to crack.*—Slight in wet season.
*Color.*—Very deep red [14. v.deep R] smoothly blending into a Moderate pink [5. m.Pk] background with a few Pale greenish yellow [104. p.gY] areas where sun protected.
Down: Moderate, short in length, does not roll up when rubbed.
Flesh:
*Color.*—Pinkish white [9. pkWhite] with Moderate red [15. m.R] streaking and flecking from the stone outward.
*Surface of pit cavity.*—Very tight freestone with Moderate red [15. m.R] fibers.
*Amygdalin.*—Scarce.
*Juice.*—Abundant, rich.
*Texture.*—Firm, tough and melting.
*Fibers.*—Abundant, fine and tender.
*Ripens.*—Slightly earliest at the apex and along the suture.
*Flavor.*—Very sweet, sub-acid, typically 18 brix.
*Aroma.*—Very slight.
*Eating quality.*—Excellent.

STONE

Type: Freestone.
Form: Oval.
Hilum: Narrow, oblong.
Base: Oblique.
Apex: Acute, with an average base angle of 80 degrees and a ⅛" [2.4 mm.] tip.
Sides: Equal.
Surface: Irregularly furrowed near the apex and pitted toward the base.
Ridges: Jagged toward the base.
External color: Dark reddish brown [44. d.rBr].
Pit wall color when cracked: Light brown [57. l.Br].
Cavity surface color: Deep yellowish brown [75. deep yBr].
Average pit wall thickness: ¼" [6.4 mm.].
Average width: 1⅛" [28.6 mm.].
Average length: 1½" [38.1 mm.].
Average breadth: ¾" [19.1 mm.].
Tendency to split: Slight.
Kernel:
*Form.*—Oval.
*Skin color.*—Pale yellow [89. p.Y] when first removed.
*Pellicle color.*—Light grayish yellowish brown [79. l.gy.yBr].
*Vein color.*—Light grayish yellowish brown [79. l.gy.yBr] when visible.
*Taste.*—Bitter.
*Viable.*—Yes.
*Average width.*—9/16" [14.3 mm.].
*Average length.*—13/16" [20.6 mm.].
*Amygdalin.*—Abundant.

USE

Market: Fresh market and long distance shipping.
Keeping quality: Good. Fruit quality observed to remain in good condition in after 17 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to its selected pollen parent, 'Snow Princess' (U.S. Plant Pat. No. 12,570) white flesh peach, by producing peaches that are freestone in type, mostly red in skin color, white with some red streaking in flesh color, firm in texture, and sub-acid in flavor, but is distinguished therefrom by having many more double blossoms and by producing peaches that are comparatively smaller in size, sweeter in flavor, and mature about fifteen days later.

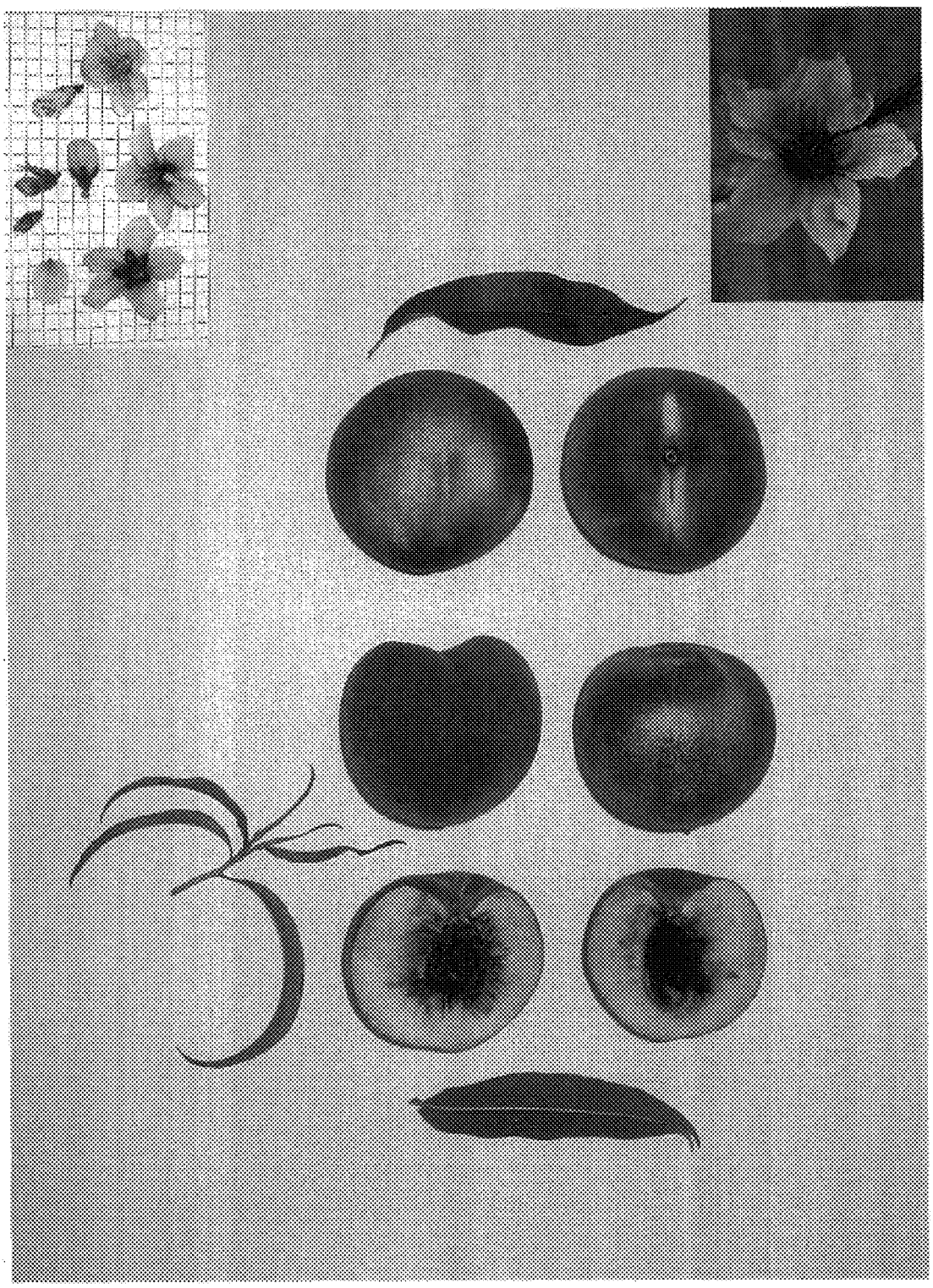

* * * * *